United States Patent [19]

Kourilsky et al.

[11] Patent Number: 5,605,800
[45] Date of Patent: Feb. 25, 1997

[54] METHOD OF DETECTING AND CHARACTERIZING A NUCLEIC ACID OR A SEQUENCE OF THE LATTER, AND ENZYMATIC REACTANT FOR THE APPLICATION OF THIS METHOD

[75] Inventors: Philippe Kourilsky; Stratis Avrameas; Brigitte Cami, born Contamine; Jean-Luc Guesdon, all of Paris, France

[73] Assignee: Institut Pasteur, Paris, France

[21] Appl. No.: 471,462

[22] Filed: Jun. 6, 1995

Related U.S. Application Data

[63] Continuation of Ser. No. 940,750, Sep. 8, 1992, which is a continuation of Ser. No. 826,631, Jan. 23, 1992, abandoned, which is a continuation of Ser. No. 715,854, Jan. 17, 1991, abandoned, which is a continuation of Ser. No. 513,040, Apr. 23, 1990, abandoned, which is a continuation of Ser. No. 353,177, May 16, 1989, abandoned, which is a continuation of Ser. No. 848,239, Apr. 4, 1986, abandoned, which is a division of Ser. No. 373,017, Apr. 29, 1982, Pat. No. 4,581,333, which is a continuation of Ser. No. 169,370, Jul. 16, 1980, abandoned, which is a continuation of Ser. No. 29,735, Apr. 13, 1979, abandoned.

[30] Foreign Application Priority Data

Apr. 13, 1978 [FR] France .................... 7810975

[51] Int. Cl.$^6$ .................................... C12Q 1/68
[52] U.S. Cl. ................. 435/6; 436/501; 536/24.3; 536/26.6; 536/25.32
[58] Field of Search .................. 435/6; 436/501; 536/24.3, 26.6, 25.32

[56] References Cited

U.S. PATENT DOCUMENTS

| | | | |
|---|---|---|---|
| 3,654,090 | 4/1972 | Schuurs et al. | 195/103.5 |
| 3,817,837 | 6/1974 | Rubenstein et al. | 435/7.9 |
| 3,839,153 | 10/1974 | Schuurs et al. | 195/103.5 R |
| 3,850,752 | 11/1974 | Schuurs et al. | 195/103.5 R |
| 3,879,262 | 4/1975 | Schuurs et al. | 195/63 |
| 3,880,934 | 4/1975 | Rammler | 260/613 D |
| 4,002,532 | 1/1977 | Weltman et al. | 435/7.95 |
| 4,016,043 | 4/1977 | Schuurs et al. | 195/103.5 R |
| 4,067,774 | 1/1978 | Rubenstein et al. | 435/188 |
| 4,134,792 | 1/1979 | Boguslaski et al. | 195/99 |
| 4,139,346 | 2/1979 | Rabbani | 422/56 |
| 4,228,237 | 10/1980 | Hevey et al. | 435/5 |
| 4,318,980 | 3/1982 | Boguslaski et al. | 435/7.5 |
| 4,358,535 | 11/1982 | Falkow et al. | 435/5 |
| 4,442,204 | 4/1984 | Greenquist et al. | 435/7 |
| 4,526,871 | 7/1985 | Avrameas et al. | 435/7.25 |
| 4,581,333 | 4/1986 | Kourilsky et al. | 435/6 |

FOREIGN PATENT DOCUMENTS

| | | |
|---|---|---|
| 0128018A2 | 12/1984 | European Pat. Off. . |
| 0155854A3 | 9/1985 | European Pat. Off. . |
| 0187332B1 | 7/1986 | European Pat. Off. . |
| 0225807A2 | 6/1987 | European Pat. Off. . |
| 2618419 | 11/1976 | Germany . |
| 2019408 | 10/1979 | United Kingdom . |

OTHER PUBLICATIONS

Kato et al., "New Technology For Enzyme Use," Chemistry and Organisms, 14(11): 737–744 (1976) and English translation.

Schuurs et al., Clinica Chimica Acta, 81:1–40 1977.

Broker et al., Nucleic Acids Res., 5(2):363–384 Feb. 1978.

Kato et al. "New Technology For Enzyme Use," Chemistry and Organisms, 14(11):737–744 (1976) and English translation.

Andres, G., et al., "Immunologic Techniques for the Identification of Antigens or Antibodies by Electron Microscopy," in Cellular Immunology (2d ed.), vol. 2, Weir (ed.), Blackwell Scientific Publications, Oxford, pp. 34.1–34.45 (1973).

Avrameas, S., "Coupling of Enzymes to Proteins with Glutaraldehyde. Use of the Conjugates for the Detection of Antigens and Antibodies," Immunochemistry 6:43–52 (1969).

Kourilsky, P., et al., "Hybridization on Filters with Competitor DNA in the Liquid Phase in a Standard and a Micro–Assay," Biochimie 56:1215–1221 (1974).

Avrameas, S., et al., "The Study of Lymphocyte Membranes Using Immunoenzymatic Techniques," in Immunofluorescence and Related Staining Techniques, Knapp et al. (eds.), Elsevier/North–Holland Biomedical Press, Amsterdam/New York, pp. 203–213 (1978).

Bauman, J., "Cytochemical Detection of Specific Nucleic Acid Sequences: Development and Application of In Situ Hybridization Methods For Fluorescence Microscopy," Drukkerij J. H. Pasmans b.v. 's Gravenhage (1980).

Bayer, E., et al., "Affinity Cytochemistry: The Localization of Lectin and Antibody Receptors on Erythrocytes Via the Avidin–Biotin Complex," FEBS Letters 68(2):240–244 (1976).

Sodja, A., Davidson, N., "Gene Mapping and Gene Enrichment by the Avidin–Biotin Interaction: Use of Cytochrome–C as a Polyamine Bridge," Nucleic Acids Research 5(2): 385–401 (1978).

Broker, T., et al., "Electron Microscopic Visualization of tRNA Genes with Ferritin–Avidin:Biotin Labels," Nucleic Acids Research 5(2):363–382 (1978).

Dale, R., et al., "Conversion of Covalently Mercurated Nucleic Acids to Tritiated and Halogenated Derivatives," Nucleic Acids Research 2(6): 915–930 (1975).

Dale, R., et al., "Direct Covalent Mercuration of Nucleotides and Polynucleotides," Biochemistry 14(11):2447–2457 (Apr.–Jun. 1975).

(List continued on next page.)

Primary Examiner—Scott W. Houtteman
Attorney, Agent, or Firm—Finnegan, Henderson, Farabow, Garrett & Dunner, L.L.P.

[57] ABSTRACT

Detection methods and compositions of matter comprising an enzyme coupled to a nucleic acid are disclosed. A complex of the enzyme-nucleic acid hybridized to a nucleic acid to be detected is also disclosed. The nucleic acid is detected by measuring the activity of the enzyme.

28 Claims, No Drawings

OTHER PUBLICATIONS

Dale, R., et al., "The Synthesis and Enzymatic Polymerization of Nucleotides Containing Mercury: Potential Tools for Nucleic Acid Sequencing and Structural Analysis," Proc. Nat. Acad. Sci. 70(8):2238–2242 (1973).

Heggeness, M., Ash J., "Use of the Avidin–Biotin Complex for the Localization of Actin and Myosin with Fluorescence Microscopy," J. Cell Biol. 73:783–788 (1977).

Heitzmann, H., Richards, F., "Use of the Avidin–Biotin Complex for Specific Staining of Biological Membranes in Electron Microscopy," Proc. Nat. Acad. Sci. 71(9):3537–3541 (1974).

Kohne, E., et al., "Room Temperature Method for Increasing the Rate of DNA Reassociation by Many Thousandfold: The Phenol Emulsion Reassociation Technique," Biochemistry 16(24):5329–5341 (1977).

Kraehenbuhl, J., et al., "Quantitative Immunocytochemistry at the Electron Microscope," in Immunofluorescence and Related Staining Techniques, Knapp et al. (eds.), Elsevier/North–Holland Biomedical Press, Amsterdam/New York pp. 245–253 (1978).

Mackey, J., et al., "Do Highly Oncogenic Group A Human Adenoviruses Cause Human Cancer? Analysis of Human Tumors for Adenovirus 12 Transforming DNA Sequences," Proc. Nat. Acad. Sci. 73(12):4657–4661 (1976).

Miller, G., et al., "Biological Properties and Viral Surface Antigens of Burkitt Lymphoma—and Mononucleosis–Derived Strains of Epstein–Barr Virus Released from Transformed Marmoset Cells," J. Virol. 18(3):1071–1080 (1976).

Molday, R., et al., "Latex Spheres as Markers for Studies of Cell Surface Receptors by Scanning Electron Microscopy," Nature 249:81–83 (1974).

Nakane, P., Wilson, M., "Cytochemical Localization of Poly–adenylic Acid (Poly A)," J. Cell. Biol. 67:302(a) (1975).

Nakane, P., Pierce, G., "Enzyme–Labeled Antibodies for the Light and Electron Microscopic Localization of Tissue Antigens," J. Cell Biol. 33:307–318 (1967).

Nakane, P., et al., "Peroxidase–Labeled Antibody: A New Method of Conjugation," J. Histochem. and Cytochem. 22(12): 1084–1091 (1974).

Reiser, J., et al., "Transfer of Small DNA Fragments from Polyacrylamide Gels to Diazobenzyloxymethyl–Paper and Detection by Hybridization with DNA Probes," Biochem. and Biophys. Res. Comm. 85(3):1104–1112 (1978).

Reitz, M., et al., "Primate Type–C Virus Nucleic Acid Sequences (Woolly Monkey and Baboon Types) in Tissues from a Patient with Acute Myelogenous Leukemia and in Viruses Isolated from Cultured Cells of the Same Patient," Proc. Nat. Acad. Sci. 73(6):2113–2117 (1976).

Rudkin, G., Stollar, B., "High Resolution Detection of DNA–RNA In Situ by Indirect Immunofluorescence," Nature 265:472–473 (1977).

Southern, E., "Detection of Specific Sequences Among DNA Fragments Separated by Gel Electrophoresis," J. Mol. Biol. 98(93):503–517 (1975).

Turler, H., "Interactions of Polyoma and Mouse DNAs, IV. Time Course and Extent of Integration of Polyoma DNA into Mouse DNA During Lytic Infection," J. Virol. 23(2):272–285 (1977).

Werner, B., et al., "Association of E Antigen with Dane Particle DNA in Sera from Asymptomatic Carriers of Hepatitis B Surface Antigen," Proc. Nat. Acad. Sci. 74(5):2149–2151 (1977).

Wilson, M., Nakane, P., "Recent Developments in the Periodate Method of Conjugating Horseradish Peroxidase (HRPO) to Antibodies," in Immunofluorescence and Related Staining Techniques, Knapp et al. (eds.), Elsevier/North–Holland Biomedical Press, Amsterdam, pp. 215–224 (1978).

Wisdom, G., "Enzyme–Immunoassay," Clinical Chemistry 22(8):1243–1255 (1976).

Yen, P., et al., "Sequence Arrangement of tRNA Genes on a Fragment of Drosophila melanogaster DNA Cloned in *E. coli*," Cell 11:763–777 (1977).

Ames, B. N., et al., "Epoxides of Carcinogenic Polycyclic Hydrocarbons are Frameshift Mutagens," Science, 176: 47–49 (1972).

Avrameas, S., et al., "Peroxidase Labelled Antibody and Fab Conjugates with Enhanced Intracellular Penetration," Immunochemistry, 8:1175–1179 (1971).

Avrameas, S., et al., "Coupling of Enzymes to Antibodies and Antigens," Scand. J. Immunol., 8, Suppl. 7:7–23 (1978).

Bloomfield, V. A., et al., Physical Chemistry of Nucleic Acids, pp. 429–476 (Harper & Row, New York, 1974).

Cain, B. F., et al., "Potential Antitumor Agents. 28. Deoxyribonucleic Acid Polyintercalating Agents," Journal of Medicinal Chemistry, 21(7): 658–668 (1978).

Canellakis, E. S., et al., "Diacridines: Bifunctional Intercalators. I. Chemistry, Physical Chemistry And Growth Inhibitory Properties," Biochimica et Biophysica Acta, 418:277–289 (1976).

Dervan, P. B., et al., "Molecular Recognition of DNA by Small Molecules. Synthesis of Bis(methidium) spermine, a DNA Polyintercalating Molecule," Journal of the American Chemical Society, 100(6):1968–1970 (1978).

Dow, L. W., et al., "In Vitro Synthesis of DNA Components of Human Genes for Globin: Use as a Probe for Messenger RNA (mRNA)," Journal of Clinical Investigation, 51: 24a–25a (1972).

Dunn, A. R., et al., "A Novel Method to Map Transcripts: Evidence for Homology Between an Adenovirus mRNA and Discrete Multiple Regions of the Viral Genome," Cell, 12: 23–36 (1977).

Festy, B., et al., "A New DNA Intercalating Drug: Methoxy–9–Ellipticine," FEBS Letters, 17(2): 321–323 (1971).

Gaugin, B., et al., "DNA Bifunctional Intercalators. 2. Fluorescence Properties and DNA Binding Interaction of an Ethidium Homodimer and an Acridine Ethidium Heterodimer," Biochemistry, 17(24): 5078–5088 (1978).

Grunstein, M., et al., "Colony Hybridization: A Method for the Isolation of Cloned DNAs that Contain a Specific Gene," Proc. Natl. Acad. Sci. USA, 72: 3961–3965 (1975).

Guesdon, J.–L., et al., "Magnetic Solid Phase Enzyme–Immunoassay," Immunochemistry, 14: 443–447 (1977).

Guesdon, J.–L., et al., "Magnetic Enzyme Immunoassay of Anti–Grass Pollen Specific IgE in Human Sera," Clin. Exp. Immunol., 33: 430–436 (1978).

Guesdon, J.–L., et al., "Magnetically Responsive Polyacrylamide Agarose Beads for the Preparation of Immunoabsorbents," Journal of Immunological Methods, 21:59–63 (1978).

Harter, M. L., et al., "Excited Sites and Photobiological Properties of Potential DNA Cross–Linking Agents, the Benzodipyrones," Photochemistry and Photobiology, 20: 407–413 (1974).

Hofmann, K., et al., "Avidin–Biotin Affinity Columns. General Methods for Attaching Biotin to Peptides and Proteins," J. Am. Chem. Soc., 100(11): 3585–3590 (1978).

Isaacs, S. T., et al., "Synthesis and Characterization of New Psoralen Derivatives with Superior Photoreactivity with DNA and RNA," Biochemistry, 16(6): 1058–1064 (1977).

Kennedy, J. H., et al., "Protein—Protein Coupling Reactions and the Applications of Protein Conjugates," Clinica Chimica Acta, 70: 1–31 (1976).

Kohn, K. W., et al., "Intercalative Binding of Ellipticine to DNA," Cancer Research, 35: 71–76 (1975).

Kohne, D. E., et al., "Room Temperature Method for Increasing the Rate of DNA Reassociation by Many Thousandfold: The Phenol Emulsion Reassociation Technique," Biochemistry, 16(24): 5329–5341 (1977).

Le Pecq, J.–B., et al., "A New Antitumoral Agent: 9–Hydroxyellipticine. Possibility of a Rational Design of Anticancerous Drugs in the Series of DNA Intercalating Drugs," Proc. Natl. Acad. Sci. USA, 71(12): 5078–5082 (1974).

Le Pecq, J.–B., et al., "DNA Polyintercalating Drugs: DNA Binding of Diacridine Derivatives," Proc. Nat. Acad. Sci. USA, 72(8): 2915–2919 (1975).

Marciani, S., et al., "Light Scattering and Flow Dichroism Studies on DNA After the Photoreaction with Psoralen," Z. Naturforsch. 27b: 196–200 (1975).

Marx, J. N., et al., "Synthesis of Some Benzodipyrones, Potential Photochemical DNA Crosslinking Agents," J. Het. Chem., 12: 417–419 (1975).

Miller, E. C., et al., "Nucleic Acid Guanine: Reaction with the Carcinogen N–Acetoxy–2–Acetylaminofluorene," Science, 153: 1125–1127 (1966).

Othman, T., et al., "Dosage Enzymoimmunologique Des Anticorps Humains Anti–Candida Albicans En Utilisant Des Perles De Polyacrylamide Agarose Magnetiques," Bull. Soc. Mycol. Med., 7(2): 249–253 (1978).

Pellegrini, M., et al., "Application of the Avidin–Biotin Method of Gene Enrichment to the Isolation of Long Double–Stranded DNA Containing Specific Gene Sequences," Nucleic Acids Research, 4(9): 2961–2973 (1977).

Reiser, J., et al., "Transfer of Small DNA Fragments from Polyacrylamide Gels to Diazobenzyloxymethyl–Paper and Detection by Hybridization with DNA Probes," Biochemical and Biophysical Research Communications, 85(3): 1104–1112 (1978).

Schuurs, A.H.W.M., et al., "Enzyme–Immunoassay," Clinica Chimica Acta, 81: 1–40 (1977).

Swack, J. A., et al., "Use of Avidin–Sepharose to Isolate and Identify Biotin Polypeptides from Crude Extracts," Analytical Biochemistry, 87: 114–126 (1978).

Van Weeman, B. K., et al., "Immunoassay Using Antigen–Enzyme Conjugates," FEBS Letters, 15(3): 232–236 (1971).

Wakelin, L. P. G., et al., "Structural Limitations on the Bifunctional Intercalation of Diacridines into DNA," Biochemistry, 17(23): 5057–5063 (1978).

Waring, M. J., et al., "Echinomycin: A Bifunctional Intercalating Antibiotic," Nature, 252: 653–657 (1974).

Wilson, W. D., et al., "Coralyne. Intercalation with DNA as a Possible Mechanism of Antileukemic Action," Journal of Medicinal Chemistry, 19(10): 1261–1263 (1976).

Wu, M., et al., "A Technique for Mapping Transfer RNA Genes by Electron Microscopy of Hybrids of Ferritin–labeled Transfer RNA and DNA: The $\phi 80hps^{u^+}$ System," J. Mol. Biol., 78:1–21 (1973).

Wu, M., et al., "Physical Mapping of the Transfer RNA Genes on $\lambda 80dglyTsu^+$," J. Mol. Biol., 78: 23–34 (1973).

Wu, M., et al., "Secondary Structure in Transfer RNA Genes," J. Mol. Biol., 78: 35–41 (1973). New Techniques for Using Enzymes, KASEAA, 14(11): 737–744 (1976).

Manning et al., Biochemistry, 16(7):1364–1370 (1977).

Manning et al., Chromosoma (Berl.), 53:107–117 (1975).

Noyes et al., Cell, 5:301–310 1975.

Wetmur, Biopolymers, 14:2517–2524 (1975).

Schuurs et al., Clinica Chimica Acta, 81:1–40 1977.

Broker et al., Nucleic Acids Res., 5(2): 363–384 Feb. 1978.

METHOD OF DETECTING AND CHARACTERIZING A NUCLEIC ACID OR A SEQUENCE OF THE LATTER, AND ENZYMATIC REACTANT FOR THE APPLICATION OF THIS METHOD

This is a continuation of application Ser. No. 07/940,750, filed Sep. 8, 1992 which is a continuation of application Ser. No. 07/826,631, filed Jan. 23, 1992, now abandoned, which is a continuation of U.S. application Ser. No. 07/715,854, filed Jun. 17, 1991, now abandoned, which is a continuation of U.S. application Ser. No. 07/513,040, filed Apr. 23, 1990, now abandoned, which is a continuation of U.S. application Ser. No. 07/353,177, filed May 16, 1989, now abandoned, which is a continuation of U.S. application Ser. No. 06/848, 239, filed Apr. 4, 1986, now abandoned, which is a divisional of U.S. application Ser. No. 06/373,017, filed Apr. 29, 1982, issued as U.S. Pat. No. 4,581,333, which is a continuation of U.S. application Ser. No. 169,370, filed Jul. 16, 1980, now abandoned, which is a continuation of U.S. application Ser. No. 029,735, filed Apr. 13, 1979, now abandoned.

The invention relates to a method for detecting the presence and, if necessary, characterizing a nucleic acid or a sequence of the latter in a specimen which can contain it. It relates also to the reactants necessary for the application of this method. Finally it relates also to the application of such a method, among other possible applications, to the rapid in vitro diagnosis of the presence in a biological specimen, derived notably from a human or animal host, of particular nucleic particles, for example infectious in nature, or again the integrity or not of this or that particular gene belonging to the normal genetic patrimony of the host.

It is not necessary to dwell on the extraordinary richness in various nucleic acids which any biological specimen can contain, for example blood, which it is possible to sample from any living creature. It is also the same regarding different sequences, for example, of numerous genes which any particular nucleic acid may contain in this specimen; whence the immense difficulties that the genetician may encounter at the level of the detection or characterization of certain nucleic acids in a specimen, difficulties which also arise as soon as there is a question of characterizing the presence of certain fragments, for example of genes, contained in these nucleic acids.

The characterization of a particular nucleic acid or of particular genes—for example for the study of the organization of genetic sequences of DNA which contains them—hence involves the production previously from the medium studied, of a fraction enriched in this nucleic acid. To this end, there have already been proposed enrichment techniques exploiting hybridation reactions between the nucleic acid or the gene sought and a probe, to the extent that the latter was available and when the hybrids formed could then be separated from the medium, for example by differential sedimentation in a solution subjected to ultra-centrifugation.

Such probes have already been described: they are generally constituted by ribonucleic acids (RNA, DNA), such as the RNA obtained in the course of the genetic transcription of the structural genes contained in the desoxynucleic acids (DNA) of the cellular organisms from which they originate, these RNA being then capable of being themselves "translated" into proteins capable of being coded by these structural genes. It is known that these RNA have sequences of nucleotides complementary to those of the DNA from which they are derived, this complementarity being manifested by the capacity possessed by these RNA to form mixed hybrids with corresponding sequences of these DNA previously denatured, inasmuch as the latter were initially bi-catenary, for example after incubation in a high ionic strength medium and at a high temperature or in a basic medium.

It has been suggested to have recourse, for marking the hybrids formed, to radioactive labeling either of the genes themselves, or of the RNA probes. These techniques are however difficult to put into practice and, in addition, do not always enable satisfactory localization of the genes concerned in their DNA.

It is with the object of permitting easier localization of the genes under study in the DNA containing them, and of promoting a method of obtaining fractions enriched in predetermined segments of DNA from these same DNA that Wanning et al. proposed a physico-chemical detection technique for these genes, consisting of chemically modifying the RNA probe, by fixing biotin groups to the latter, through bridges formed by groups derived from cytochrome C and fixing physical marks visible with the scanning (electron) microscope, to the DNA, after hybridization with the probe, formed by submicroscopic spheres having diameters of about of 60 nm, notably based on poly(methacrylate), previously modified chemically and coupled in covalent manner to avidin molecules (notably in the articles entitled "A New Method of in situ Hybridization", *Chromosoma (Berl.)* 53. 107–117 (1975), Springer-Verlag 1975 and "A Method for Gene Enrichment Based on the Avidin-Biotin Interaction. Application to the Drosophila Ribosomal RNA Genes", *Biochemistry*, Vol. 16, No. 7, 1364–1369, 1977).

In fact, the incubation of hybrids modified with biotin in the presence of submicroscopic spheres modified with avidin permits the "labeling" and makes locatable the positions of the desired genes in the DNA which contains them, with respect to the overall structure also visible in the electronic microscope of this DNA, due to the fact of the very powerful non-covalent interactions which are then produced between the sites remaining free of the biotin and of the avidin.

This method however is hardly applicable to the purposes of rapid detection of the presence or absence of such genes and of such DNA in a biological specimen derived from a human or animal host, for example with the object of establishing rapid diagnosis either of the disease with which the host may possibly be afflicted, or of the integrity or not of a gene or of a DNA sequence, for example, in this host.

The invention arises from the conversion of the Manning et coll. method, which conversion leads to techniques of detection, even of characterization, capable of being applied in the absence of expensive equipment, by persons having only little laboratory experience.

The method of detection according to the invention of the possible presence or of the characterization of a sequence or particular fragment of nucleic acid, notably of a gene, even of the whole nucleic acid in a complex sample of nucleic acids, by contacting the sample, if necessary after prior denaturation of the nucleic acid under study, with a probe comprising a complementary nucleic acid, capable of being hybridized with the nucleic acid sequence or the nucleic acid sought, is characterized in that the reagent or probe used is a p robe modified chemically by coupling or for its coupling with an enzyme prior or subsequent to the hybridization reaction, the possible presence of nucleic acid sequence or of the nucleic acid sought being revealable by the action of the thus-transformed hybridization product of the probe and of the sequence or of the nucleic acid sought, on an enzyme substrate.

Advantageously, the enzyme is selected according to its capacity to act on a chromogen substrate, which permits the measurement by optical or similar analysis, of the conversion ratio of the substrate, which ratio is then correlatable with the presence or not of the nucleic acid sequence or of the nucleic acid sought in the initial sample.

In a preferred embodiment of the application of the invention, the probe is modified by a chemical group capable of forming a stable complex with the enzyme or a molecule itself bound stably to the enzyme. Advantageously, the above-said chemical group and the above-said molecule are respectively constituted by biotin and avidin or vice versa, the enzyme being itself advantageously constituted by β-galactosidase.

It is self-evident that the chemical modification must be such that it does not prevent the possible subsequent hybridization of the probe with the DNA sequence or fragment sought.

It will immediately appear to the specialist that this technique permits a rapid determination of the presence or not in a biological sample of the gene or DNA fragment corresponding to the probe used, and this even in the presence of a considerable amount of other nucleic acids. This is particularly so due to the fact of the amplification at the level of detection which is obtained by the action of the enzyme fixed to the hybrid on the substrate brought into its presence. It is even possible, after sufficient purification of the hybrid, to obtain an indication as to the concentration in the DNA sought in the biological samples studied or as to the distribution ratio of the gene sought in a purified DNA, by measurement of the enzymatic activity observed.

Starting from a nucleic acid sample to be studied, it is possible to first carry out the hybridization, then the coupling reaction between the chemically modified and hybridized probe, on the one hand, of the enzyme, on the other hand, to then proceed with the separation or the degradation of the possible excess of non-hybridized probe and of the excess enzyme which has not reacted with the probe, before carrying out the above mentioned measurement.

As an alternative, the separation or degradation of the possible excess of non-hybridized probe may be carried out before the coupling reaction between the chemically modified and hybridized probe, on the one hand, and the enzyme, on the other hand.

The specific probe can be constituted by any specific RNA or DNA either single strand (mono-catenary), or denaturated previously by techniques known per se, if it relates to a DNA (or an RNA) initially double strand.

When the chemical modification of the probe is carried out by means of biotin, it is possible to resort to the technique described by Manning et coll. in the already mentioned publications, through cytochrome C, notably in the proportion of one molecule of biotin on the average for about 100 nucleotides.

Advantageously, recourse is then had for labeling the hybrid by the enzyme, to the product resulting from the coupling of avidin and the enzyme, notably β-galactosidase, by the Avrameas method ("Immunochemistry", 1969, 6, 43–52).

It goes without saying that it is possible to resort to other chemical modifications of the probe and, if necessary, of the enzyme, to effect their coupling, preferably after the hybridization reaction, and that it is possible to reverse the modifying agents of the probe and of the enzyme respectively.

Other pairs of modifying agents of the probe on the one hand, and of the enzyme, on the other hand, may also be used. By way of example, the following pairs are mentioned, the first of these agents being preferably used for the chemical modification of the probe and the second for the chemical modification of the enzyme. For example, the probe may be modified, by a known method, by metallic ions (mercury for example) and the development is done by means of an enzyme having hydrosulphide groups (—SH), or coupled to a support including such groups.

By way of example, which is of course non-limiting, of an experimental procedure which may be applied in the case where the sample to be analyzed is constituted by a blood specimen of some millileters, it is possible to operate as follows:

The blood cells are first lysed and the DNA is extracted therefrom by a conventional technique.

A small amount of the DNA obtained, for example comprised between 1 and 100 μg, is denatured by 0.1 to 0.3N soda, the solution then being neutralized and brought back to pH 7.

To the solution obtained, the probe corresponding to the DNA fragment or to the DNA sought is then added in the proportion of about 1 μg of probe per 100 μg of denatured DNA (the amount of soda to be used is a function of the proportion of DNA sought in the specimen to be analyzed). The solution is then completed with salts for conferring on the medium a high ionic force, at least 0.3M NaCl, in the presence of 50% formamide and a chelating agent at low concentration, preferably in small volume. The hybridization can then be carried out at ordinary temperature for 1 to 40 hours (generally overnight). It is also possible to use the technique already described by Manning. As an alternative, any other hybridization technique can also be resorted to, for example, that described by KOHNE et al in "Biochemistry" (1977) (16, 5329–5341), at ordinary temperature in a phenol emulsion.

Avidin coupled to an enzyme such as β-galactosidase is then added to the medium under conditions permitting the coupling of the biotin of the probe with the free groups of the avidin of the coupling compound of the avidin and the enzyme.

The non-hybridized reagent is then separated from the hybridized reagent by conventional techniques, such as precipitation with polyethylene glycol, passage over gel, for example that of the type named SEPHAROSE, ultra-centrifugation, etc.

As an alternative it is also possible to carry out the separation of the non-hybridized probe before the coupling of the avidin bearing the enzyme with the biotin groups coupled to the hybridized probe with the DNA.

The enzyme possibly fixed and consequently the possible effective hybridization of the probe with the DNA studied may be visualized or detected by placing in contact with the medium a substrate of the enzyme, notably that constituted by orthonitrophenol galactoside (ONPG).

It is self-evident that the experimental conditions once well-fixed, it is possible to determine a measurable activity threshold, for example, by a colorimetric or fluorographic technique, beyond which it is possible to conclude in the presence in the treated sample of DNA or of the DNA fragments sought.

The following description of a test carried out in the laboratory has simply the purpose of illustrating the manner in which the process according to the invention may be put into practice, it being obviously understood that the modifications at the level of techniques, according to the nature of the biological specimen studied and of that of the DNA or of the DNA fragment sought, are within the evident scope of the technician skilled in the art.

Experiments were carried out on the model consisting of detecting the presence of a mouse DNA by hybridization of this DNA with a mouse ribosomic RNA used as a probe.

Mouse DNA (100 μg per 100 μl of aqueous solution) ions denatured by addition of soda (10 μl of 1M NaOH). 10 minutes later, the solution was brought back to pH neutral by the addition of 10 μl of 1.5M acid sodium phosphate NaH$_2$PO$_4$.

1 μg of ribosomic RNA labeled with biotin by means of cytochrome C, prepared by the technique of Manning & Coll., is added to the denatured DNA solution. The volume was adjusted to 160 μl with water. 40 μl of a solution having a concentration of mineral salts equal to twenty times that of the solution called SSC (abbreviation of the English expression "standard saline citrate") and 200 μl of redistilled or deionized formamide was then added to the medium. It is recalled that the SSC solution is an aqueous solution of 0.15M sodium chloride, 0.015M sodium citrate, at pH 7.0.

The mixture was incubated until the next day at ordinary temperature, then dialyzed at 4° C. against a solution having a double concentration of the SSC solution, then for 8 hours against 500 ml of a phosphate buffer at pH 7.0 containing phosphate at a concentration of 0.1M, sodium chloride at a concentration of 1M and ethylene-diamine-tetrasodium acetate (EDTA) at a concentration of 0.01M. The latter dialysis is then repeated twice, each time for 8 hours.

The solution thus-obtained was treated with pancreatic ribonuclease for 1 hour at ordinary temperature, to obtain a final concentration of 10 μg per ml of ribonuclease, this treatment permitting the degradation of the non-hybridized RNA.

To the medium obtained was then added a solution of cytochrome C (1 mg per ml) and 1 microliter of a solution containing 1 mg per ml of avidin and 2 mg per ml of β-galactosidase, of which 1 molecule of β-galactosidase in seven is coupled with avidin. It is mixed and the solution is then left to stand at 4° C. for 4 hours. The medium was then diluted to 10 ml with the phosphate dialysis buffer and the solution obtained is subjected to ultracentrifugation for 1 hour at 35,000 rpm (in a BECKMAN ROTOR SW 41 centrifuge). The DNA and the hybridized RNA are to be found in the centrifugation culot, as well as the avidin β-galactosidase bound to this RNA. The supernatant liquor contains the non-hybridized RNA degraded by the ribonuclease and the unbound avidin β-galactosidase.

The culot is collected and resuspended in 10 ml of buffer. It is recentrifuged and the culot is taken up again in 0.5 ml of buffer (tube No. 1) and the activity of the β-galactosidase on the ONPG substrate is assayed by the technique described by Miller ("Experiments in bacterial genetics, 1972, Cold Spring Harbor Laboratory", Cold Spring Harbor, N.Y., USA), by measurement of the optical density of the medium at 420 mp, after incubation of the medium at 37° C. for 30 minutes or more.

Controls are prepared under conditions strictly identical with those which have been described above, except that in a first case the initial addition of ribosomic RNA (tube No. 2) was omitted and in the other case the addition of mouse DNA (tube No. 3) was omitted.

The results of the three assays carried out are shown in the table below:

| Tube No. | Contents | | Result of the assay (optical density at 420 mu after 30 minutes at 37° C.) |
|---|---|---|---|
| | DNA | RNA | |
| 1 | + | + | 0.45 |
| 2 | + | − | 0.14 |
| 3 | − | + | 0.15 |

The signs + and −, respectively in the columns under the headings DNA and RNA, signify the presence or absence either of DNA, or of RNA, in the initial medium.

As can be observed on examining this table, the optical density measured in tube No. 1 (containing the hybrid) is very significantly greater than the optical densities measured in the control tubes.

The experimental model which has just been described therefore illustrates the conditions under which the possible presence of a desired DNA or DNA fragment may be detected, to the extent that a probe complementary to this DNA or to this RNA fragment is available by resorting to a simple technique requiring neither very complicated laboratory equipment nor a particularly experienced technician.

The invention is applicable particularly advantageously to in vitro diagnosis operations of the presence, for example in a biological sample (blood sample, specimen of stools, etc.) of various viruses, such as those named Herpes, Epstein Barr, virus Pox, cytomegalo, etc. In the same way, the invention may be applied to the diagnosis, for example, of specific chromosomic anomalies.

It is also applicable to the realization of bacterial diagnoses, in particular in the case where individuals are bearers of pathogenic genes, both expressed and non-expressed (or latent).

It will appear naturally to the specialist, in the case of investigating an infectious DNA, that it is possible to conclude rapidly as to the healthy character of the treated biological specimen, and having regard to the nucleic acid or the fragment of nucleic acid sought, in the absence of induction observe on the chromogenic substrate, or at least an over-shoot of the activity threshold, either predetermined experimentally, or by comparison with controls free of the virus.

Conversely, the absence of action observed with respect to the chromogenic substrate, notably beyond the above-mentioned threshold, can, in the other type of application, envisaged above by way of example, translate the presence of an anomaly of the chromosomic anomaly sought, in the absence of observed total or partial hybridization, between the probe and the DNA studied.

It is advantageously possible to pace, for example, at the disposal of medical analysis laboratories, "kits" containing all of the essential reactants for the application of the process according to the invention. These kits can, in particular, contain a sampling of probes corresponding, for example, to the DNA of the virus or bacteria, of conventionally sought pathogenic viruses or bacteria, or even of probes relating to particular genes which should normally be contained in biological specimens, notably blood specimens, under test.

In this regard, the invention relates hence to a "kit" characterized in that it comprises:

- at least one specific probe formed from RNA or a single RNA strand, characteristic of a nucleic acid sequence or of a nucleic acid to be sought, this probe being modified chemically for its coupling with an enzyme,
- said enzyme, if necessary, modified so as to be able to be coupled with said probe,
- a substrate, notably a chromogene, specific to the enzyme,
- the reactants necessary for the lysis of the cellular medium to be studied, notably a blood medium, and for the extraction of nucleic acids from the cells of this medium.

As has already been observed in the foregoing, it is advantageous to constitute the modified probe by a probe to which biotin is bound, the modified enzyme being then constituted by the enzyme itself, for example β-galactosidase, coupled to avidin.

The invention relates also moreover, by way of novel industrial product, to the coupling product of an enzyme (of which the action may be revealed with respect to a substrate, notably chromogenic) and of a probe (RNA or single strand DNA), either directly, or through a coupling agent. It relates also again to the coupling product of the enzyme and of at least one chemical molecule, the whole then being capable of being coupled in its turn with a probe (RNA or DNA), if necessary modified, itself capable of being hybridized with a DNA or a DNA fragment. By way of examples of such novel industrial products, may be mentioned the coupling products of a probe (RNA or DNA) with an enzyme, such as β-galactosidase, or again coupling products of avidin or of biotin with such an enzyme.

Of course, the invention may be applied in other fields of application, notably for the labeling of certain DNA fragments in well-known genetic experiments seeking to establish the genotype of the DNA concerned. In particular, the invention may be applied to the determination of the incorporation or not of a particular DNA fragment in experiments of genetic sorting comprising for example operations of transforming DNA from an infected cell with a foreign DNA containing the DNA fragment concerned or on the contrary operations of transduction including the incorporation of a DNA fragment concerned, normally contained in the DNA of the cell, in the DNA of the virus used for the infection of the cell, etc., to the extent that, of course, a probe constituted by the RNA fragment or DNA complementary to the sought nucleic acid fragment is available.

As is self-evident and as emerges already besides from the foregoing, the invention is in no way limited to those of its modes of application and embodiments which have been more especially envisaged; it encompasses on the contrary all modifications, notably those where recourse is had to modifications of the probe which may enable the enzymatic assay of the hybrid and modifications relating to the formation and/or purification of the hybrids, to the labeling or the chemical modification of the DNA studied itself, under conditions which have been described above, the RNA probe not being the subject of any particular labeling; such an inversion of the reactants may be envisaged, for example in the case of a DNA including numerous examples of repetetive genes, that it is desired to isolate from the whole DNA, in the form of a hybrid with a probe, after fragmentation of the DNA concerned by conventional techniques. It is self-evident that these equivalents are included within the field of protection defined by the claims.

By way of yet another modification, it is possible to have recourse to a process consisting of marking the hybrid formed by the desired DNA and the probe, by means of an anti-hybrid antibody, coupled to an enzyme such as β-galactosidase.

We claim:

1. A detection method for detecting the presence or absence of a nucleic acid sought to be detected in a biological medium, the medium containing also other nucleic acids which are not sought to be detected, by means of a probe containing a nucleic acid complementary of said nucleic acid sought to be detected and by means of measurement on a substrate specific to an enzyme, which method comprises:

coupling said probe containing said complementary nucleic acid with said enzyme, thereby forming an enzyme-bonded probe, hybridizing the nucleic acid sought to be detected with said enzyme-bonded probe, thereby forming an enzyme-bonded product, separating excess of non-hybridized enzyme-bonded probe from said enzyme-bonded product, wherein the probe or the enzyme is modified by a chemical group, measuring the activity of the enzyme-bonded product on the substrate specific to the enzyme in the presence of the other nucleic acids, thereby detecting whether or not the nucleic acid sought to be detected is present.

2. A detection method for detecting the presence or absence of a nucleic acid sought to be detected in a biological medium, the medium containing also other nucleic acids which are not sought to be detected, by means of a probe containing a nucleic acid complementary of said nucleic acid sought to be detected by means of measurement on a substrate specific to the enzyme, which method comprises:

hybridizing the nucleic acid sought to be detected with said probe containing complementary nucleic acid and being coupled to an enzyme, thereby forming a hybridized product, separating the excess of non-hybridized probe from said hybridized product and the other nucleic acids, thereby leaving an enzyme-bonded product resulting from the hybridization between the nucleic acid sought to be detected, wherein said probe is chemically coupled to said enzyme, measuring the activity of said enzyme-bonded product on a substrate specific to the enzyme in the presence of the other nucleic acids, thereby detecting whether or not the nucleic acid sought to be detected is present.

3. The method of claim 2, wherein said probe is coupled directly to the enzyme.

4. The method of claim 2, wherein the probe is chemically modified by said enzyme through a biotin or avidin complex.

5. The method of claim 2, wherein the enzyme has an —SH group.

6. The method of claim 2, wherein the enzyme is beta-galactosidase.

7. The method of claim 2, wherein the complementary nucleic acid is selected from the group consisting of DNA and RNA.

8. The method of claim 6, wherein the substrate for the enzyme is orthonitrophenol galactoside.

9. The method of claim 7, wherein the DNA or RNA is single-stranded.

10. The method of claim 2, wherein the biological medium is not enriched in the nucleic acid sought to be detected.

11. The method of claim 2, wherein the step of separating the non-hybridized probe is performed after the coupling step bonding but prior to the measuring step.

12. A detection method for detecting the presence of a nucleic acid sought to be detected in a sample by means of a nucleic acid probe comprising a nucleic acid, wherein said nucleic acid is hybridizable with said nucleic acid sought to be detected, and an enzyme coupled to said nucleic acid comprising the steps of:

hybridizing any said nucleic acid sought to be detected with said nucleic acid probe, thus forming an enzyme-bonded product;

measuring the activity of said enzyme-bonded product on a substrate specific to said enzyme; and detecting the presence of any said nucleic acid sought to be detected.

13. A method for detecting the presence or absence of a nucleic acid in a biological medium, the medium containing also other nucleic acids which are not sought to be detected, said method comprising the steps of:

hybridizing the nucleic acid sought to be detected with a complementary nucleic acid, the complementary nucleic acid modified by a chemical group for coupling with the enzyme, thereby forming a hybridized product;

coupling the chemically-modified nucleic acid, hybridized with the nucleic acid sought to be detected with said enzyme; and measuring the activity of the chemically-modified enzyme-coupled product on the substrate specific to the enzyme, thereby detecting whether or not the nucleic acid sought to be detected is present.

hybridizing the nucleic acid sought to be detected with said probe containing complementary nucleic acid and being coupled to an enzyme, thereby forming a hybridized product, separating the excess of non-hybridized probe from said hybridized product and the other nucleic acids, thereby leaving an enzyme-bonded product resulting from the hybridization between the nucleic acid sought to be detected, wherein said probe is chemically coupled to said enzyme, measuring the activity of said enzyme-bonded product on a substrate specific to the enzyme in the presence of the other nucleic acids, thereby detecting whether or not the nucleic acid sought to be detected is present.

14. A detection method for detecting the presence or absence of a nucleic acid sought to be detected in a biological medium, the medium containing also other nucleic acids which are not sought to be detected, by means of measurement of a substrate specific to a chemically-modified enzyme, which comprises:

hybridizing the nucleic acid sought to be detected with a probe coupled to a chemically-modified enzyme and having a nucleic acid complementary of the nucleic acid sought, thereby forming a hybridized chemically-modified enzyme-coupled product, separating excess non-hybridized probe from said chemically-modified enzyme-coupled product and other nucleic acids, measuring the activity of the chemically-modified enzyme-coupled product on the substrate specific to the enzyme in the presence of the other nucleic acids, thereby detecting whether or not the nucleic acid is present.

15. A composition of matter for detecting the presence or absence of a nucleic acid sought to be detected in a biological sample containing said nucleic acid and other nucleic acids, the presence or absence of which is not sought to be detected, said composition of matter comprising an enzyme chemically bonded probe, which probe comprises a complementary nucleic acid sequence which is hybridizable with the nucleic acid sought to be detected to thereby form a hybridized product enzyme complex, and a substrate specific to the enzyme for the detection of said product enzyme.

16. The composition of matter of claim 15 wherein the substrate is a chromogen.

17. The composition of matter of claim 15 further comprising the nucleic acid sought to be detected in an amount sufficient for detection by the enzyme chemically bonded probe.

18. The composition of matter of claim 15 wherein the enzyme chemically bonded probe comprises a probe chemically modified with biotin and an enzyme chemically modified with avidin, said biotin being coupled with said avidin.

19. The composition of matter of claim 15 wherein the probe and the enzyme are chemically linked through a biotin-avidin complex, the enzyme is beta-galatosidase and the substrate is orthonitrophenol galactoside.

20. A method for detecting the presence or absence, in a biological medium, of a nucleic acid which comprises a determined nucleic acid sequence, the medium containing also other nucleic acids which are not sought to be detected, by means of a probe comprising a nucleic acid sequence which is complementary to said nucleic acid sought to be detected, said method comprising the steps of:

hybridizing any said nucleic acid sought to be detected with said probe having a complementary nucleic acid, thereby forming a hybridization product with said nucleic acid sought to be detected;

separating excess of probe which is not hybridizable to said determined nucleic acid sequence, coupling the probe portion of any said hybridized product with an enzyme, thereby forming an enzyme-probe product, where either said probe is modified by a chemical group for coupling with the enzyme or said enzyme is modified by a chemical group for coupling with said probe; and measuring the activity of the enzyme-probe product on a substrate specific to the enzyme, thereby detecting whether or not the determined nucleic acid sequence is present in the biological medium.

21. A composition for determining the presence or absence of a determined nucleic acid sequence present in a biological sample, said composition comprising an enzyme, a nucleic acid which is modified by a chemical group for coupling with said enzyme and which comprises a nucleic acid sequence which is complementary to said determined nucleic acid sequence, said nucleic acid hybridized to any said determined nucleic acid sequence, forming a hybridized product-enzyme complex, and a substrate specific to the enzyme for the detection of said hybridized product-enzyme complex.

22. The composition of matter of claim 21, wherein the substrate is a chromogen.

23. The composition of matter of claim 21, wherein the chemical group is selected from the group consisting of biotin and avidin.

24. The composition of matter of claim 23, wherein the probe is modified with biotin and the enzyme with avidin.

25. A composition of matter which comprises a nucleic acid sought to be detected which is hybridized to a probe, said probe comprising a nucleic acid sequence complementary to the nucleic acid sought to be detected, wherein said hybridized probe is modified by a chemical group and said probe is bonded to an enzyme through said chemical group, said composition of matter capable of acting on a substrate specific to the enzyme.

26. The composition of matter of claim 25, wherein the substrate is a chromogen.

27. The composition of matter of claim 25, wherein the chemical group is selected from the group consisting of biotin and avidin.

28. The composition of matter of claim 27, wherein the probe is modified with biotin and the enzyme with avidin.

* * * * *

UNITED STATES PATENT AND TRADEMARK OFFICE
CERTIFICATE OF CORRECTION

PATENT NO. : 5,605,800
DATED : February 25, 1997
INVENTOR(S) : Phillippe Kourilsky, et. al.

It is certified that error appears in the above-indentified patent and that said Letters Patent is hereby corrected as shown below:

Title page, between "[45] Date of Patent : "and "Feb. 25, 1997," add--
*--.

Title page, after "[73] Assignee: Institut Pasteur, Paris, France" insert --[*] Notice: The term of this patent shall not extend beyond the eexpiration date of Pat. No. 4,581,333--.

Signed and Sealed this

Twenty-sixth Day of August, 1997

Attest:

BRUCE LEHMAN

Attesting Officer

Commissioner of Patents and Trademarks